US008637539B2

(12) United States Patent
Nagase et al.

(10) Patent No.: US 8,637,539 B2
(45) Date of Patent: Jan. 28, 2014

(54) REMEDIES FOR NEUROPATHIC PAIN AND MODEL ANIMALS OF NEUROPATHIC PAIN

(75) Inventors: Hiroshi Nagase, Kamakura (JP);
Takashi Endo, Chigasaki (JP); Kuniaki Kawamura, Kamakura (JP); Toshiaki Tanaka, Zushi (JP); Tomohiko Suzuki, Kawasaki (JP); Tsutomu Suzuki, Yokohama (JP); Yasushi Kuraishi, Nei-gun (JP); Kimiyasu Shiraki, Toyama (JP)

(73) Assignee: Toray Industries, Inc. (JP)

( * ) Notice: Subject to any disclaimer, the term of this patent is extended or adjusted under 35 U.S.C. 154(b) by 23 days.

(21) Appl. No.: 11/206,489

(22) Filed: Aug. 18, 2005

(65) Prior Publication Data
US 2006/0094741 A1 May 4, 2006

Related U.S. Application Data

(62) Division of application No. 10/049,472, filed as application No. PCT/JP00/05690 on Aug. 24, 2000, now abandoned.

(30) Foreign Application Priority Data

Aug. 24, 1999 (JP) .................................... 11/236778

(51) Int. Cl.
*A01N 43/42* (2006.01)
*A61K 31/44* (2006.01)
(52) U.S. Cl.
USPC ....................................................... 514/282
(58) Field of Classification Search
None
See application file for complete search history.

(56) References Cited

U.S. PATENT DOCUMENTS

| | | | |
|---|---|---|---|
| 5,739,145 A | 4/1998 | Nagase et al. |
| 5,776,945 A | 7/1998 | Nagase et al. |
| 5,849,731 A | 12/1998 | Nagase et al. |
| 5,852,030 A | 12/1998 | Nagase et al. |
| 6,087,369 A | 7/2000 | Nagase et al. |
| 6,147,084 A | 11/2000 | Nagase et al. |
| 6,156,762 A | 12/2000 | Nagase et al. |
| 6,172,078 B1 | 1/2001 | Nagase et al. |
| 6,177,438 B1 | 1/2001 | Nagase et al. |
| 6,187,782 B1 | 2/2001 | Nagase et al. |
| 6,277,859 B1 | 8/2001 | Nagase et al. |
| 6,291,470 B1 | 9/2001 | Nagase et al. |
| 6,316,461 B1 | 11/2001 | Nagase et al. |
| 6,323,212 B1 | 11/2001 | Nagase et al. |
| 6,440,987 B1 | 8/2002 | Nagase et al. |

FOREIGN PATENT DOCUMENTS

| | | |
|---|---|---|
| EP | 0 577 847 A1 | 1/1994 |
| EP | 0 897 726 | 2/1999 |
| WO | 01 14382 | 3/2001 |

OTHER PUBLICATIONS

Nagase et al. "Discovery of a Structurally Novel Opioid Kappa-Agonist Derived from 4,5-Epoxymorphinan", Chemical and Pharmaceutical Bulletin, 46(2), 1998:366-369.*
Pappagallo et al. "Chronic Opioid Therapy as Alternative Treatment for Post-Herpetic Neuralgia". Annals of Neurology, 35(Suppl); 1994:S54-S56.*
Hassenbusch et al. "Long-Term Intraspinal Infusions of Opioids in the Treatment of Neuropathic Pain". Journal of Pain and Symptom Management, 10(7); 1995:527-543.*
Endoh et al. "Potent Antinociceptive Effects of TRK-820, A Novel Kappa-Opioid Receptor Agonist". Life Sciences, 65(16), 1999:1685-1694.*
Osol A. [Editor] "Chapter 27: Structure-Activity Relationship and Drug Design". Remington's Pharmaceutical Sciences (Sixteenth Edition). Mack Publishing, 1980. pp. 420-435.*
Ebert et al. "Opioid Analgesics as Noncompetitive N-Methyl-D-Aspartate (NMDA) Antagonists". Biochemical Pharmacology, 56; 1998:553-559.*
Dellemijn P. "Are Opioids Effective in Relieving Neuropathic Pain'?" Pain, 1999; 80:453-462.*
Zorn et al. "Treatment of Neuropathic Pain: The Role of Unique Opioid Agents". Practical Pain Management, 2011:26-33.*
*The Merck Index*, Twelfth Edition, Susan Budavari, Editor, Merck Research Laboratories, 1996.
Leon F. Tseng et al., *Delta Opioid Receptor-Mediated Antinociceptive Properties of a Nonpeptidic Delta Opioid Receptor Agonist, (−)TAN-67, in the Mouse Spinal Cord*, Journal of Pharmacology and Experiemntal Therapeutics, vol. 280, No. 2, 1997, pp. 600-605.
Andrew Barber et al., *Review: Central & Peripheral Nervous ystems: Novel developments with selective, non-peptidic kappa-opoid receptor agonist*, Expert Opinion on Investigational Drugs, Ashley Publications, 1997, pp. 1351-1368.

(Continued)

*Primary Examiner* — Leslie A. Royds Draper
(74) *Attorney, Agent, or Firm* — DLA Piper LLP (US)

(57) ABSTRACT

The present invention relates to a therapeutic agent for neuropathic pain containing, as an active ingredient, a compound represented by general formula (I) or a pharmacologically acceptable acid addition salt thereof:

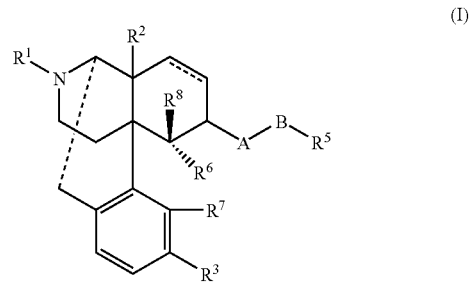

(I)

(wherein $R^1$, $R^2$, $R^3$, $R^4$, $R^5$, $R^6$, $R^7$, $R^8$, A, and B have the same definitions as those described in the specification), and an animal model produced by administering (+)-4a-(3-hydroxyphenyl)-2-methyl-1,2,3,4,4a,5,12,12a-octohydro-trans-quinolino[2,3-g]isoquinoline. The present invention makes it possible to perform drug treatment for neuropathic pain. The therapeutic effect of a compound against neuropathic pain can also be evaluated.

1 Claim, 8 Drawing Sheets

(56) References Cited

OTHER PUBLICATIONS

Catheline, G et al., "Further Evidence for a Peripheral Component in the Enhanced Antinociceptive Effect of Systemic Morphine in Mononeuropathic Rats: Involvement of κ, but not δ-opioid Receptor", *European Journal of Pharmacology*. 1996, vol. 315, pp. 135-143.

Catheline, G. et al., "Peripheral Component in the Enhanced Antinociceptive Effect of Systemic U-69,593, a κ-opioid Receptor Agonist in Mononeuropathic Rats," *European Journal of Pharmacology*, 1998, vol, 317 pp. 171-178.

Rowbotham, M.C, et al., "Both Intravenous Lidocaine and Morphine Reduce the Pain of Postherpetic Neuralgia," *Neurology*, Jul. 1991, vol. 41, pp. 1024-1028.

Watson, C.P.N. et al., "Efficacy of Oxcodone in Neuropathic Pain: A Randomized Trial in Postherpetic Neuralgia," *Neurology*, 1998, vol. 50, pp. 1837-1841.

Keita, H. et al., "Antinociceptive Effect of a κ-Opioid receptor Agonist that Minimally Crosses the Blood-Brain Barrier (ICI 204448) in a Rat Model of Neuropathy," *Eur. J. Pharmacol.*, Apr. 1995, vol. 277, issues 2-3, pp. 278-280 (one sheet—Abstract only).

\* cited by examiner

REMEDIES FOR NEUROPATHIC PAIN AND MODEL ANIMALS OF NEUROPATHIC PAIN

RELATED APPLICATION

This application is a divisional of application Ser. No. 10/049,472, filed May 28, 2002, which is a §371 of PCT/JP2000/05690, filed Aug. 24, 2000, incorporated herein by reference.

TECHNICAL FIELD

The present invention relates to therapeutic agents for neuropathic pain containing opioid κ-receptor agonist compounds as active ingredients. The present invention also relates to a neuropathic pain animal model, a method for producing the model, a method for evaluating an effective compound for treating neuropathic pain using the model, and an effective compound for treating neuropathic pain which is obtained by the evaluation method.

BACKGROUND ART

In neuropathic pain, which predominates in inveterate pain, even in the absence of stimuli to nociceptors due to tissue damage, persistent, unbearable, burning pain is caused, and in many cases, it may be complicated with paroxysmal pain. Additionally, hypoesthesia may occur in pain locations, and allodynia, in which pain is initiated by a slight stimulus which does not normally provoke pain, may often be observed. Clinically, these characteristic symptoms are mixed in the individual diseases. The International Association for the Study of Pain defines neuropathic pain as pain caused by a primary lesion or dysfunction of the nervous system, and the nervous system includes the peripheral nervous system and the central nervous system. Specifically, neuropathic pain can be related to peripheral nerve disorders (e.g., diabetes, alcoholic and other drug poisoning, and amyloidosis), amputation, posterior rhizotomy, brachial plexus avulsion injuries, spinal cord injuries, multiple sclerosis, the Parkinsonian syndrome, etc., and can be postherpetic neuralgia, central postapoplectic pain (so-called thalamic pain), etc. That is, neuropathic pain is caused by organic changes or dysfunction of the nervous system due to external injuries to the peripheral or central nervous system itself, infection, ischaemia, etc.

Morphine, which is widely used for treating pain, does not have a sufficient effect on the treatment of neuropathic pain, and also neuropathic pain is often resistant to opioid analgesics. Under the circumstances, development of effective therapeutic agents for inveterate pain including neuropathic pain has been desired. Examples of known therapeutic methods include surgical treatment, such as therapeutic spinal cord stimulation and dorsal root entry zone lesions, and chronic intrathecal administration of Baclofen, which is a γ-aminobutyric acid (GABA) receptor agonist, and ketamine, which is an N-methyl-D-aspartate (NMDA) receptor antagonist. However, since these methods are highly invasive, less invasive therapeutic methods have been desired, and thus it is important to develop new drugs effective against neuropathic pain.

On the other hand, although Japanese Patent No. 2525552 discloses morphinan derivatives having opioid κ-receptor agonist activity and analgesic action, the therapeutic effects of these compounds on neuropathic pain are not disclosed.

An animal model which shows the same clinical symptoms as those of human neuropathic pain is essential to the development of effective new drugs for neuropathic pain. Currently, with respect to the neuropathic pain animal model, although cutting and ligature of the peripheral nerve (G. J. Bennet & Y. K. Xie, Pain, 33: 87-107, 1988) or damage to the spinal cord (J. X. Hao, Pain, 45: 175-185, 1991) are conducted, complex operations must be performed for screening, and therefore, development of a simple animal model for neuropathic pain has been desired.

On the other hand, an intrathecal administration method using a rodent, particularly a mouse, is known as a method which can be performed relatively simply without anesthetization (J. L. K. Hylden & G. L. Wilcox, Eur. J. Phammacol., 67: 313-316, 1980). It has also been reported that when NMDA (L. M. Aanonsen & G. L. Wilcox, J. Pharmacol. Exp. Ther., 243: 9-19, 1987) and substance P (J. L. K. Hylden & G. L. Wilcox, Brain Res., 217: 212-215, 1981) are intrathecally administered to mice, scratching, biting, and licking behavior, namely, SBL behavior, appears, suggesting the generation of pain. It has also been reported that by intrathecally administering (+)-4a-(3-hydroxyphenyl)-2-methyl-1,2,3,4,4a,5,12,12a-octahydro-trans-quinolino[2,3-g]isoquinoline to mice, hyperalgesia is generated (L. F. Tseng et al., J. Pharmacol. Exp. Ther., 280: 600-605, 1997). However, these animal models are exhibited as drug-induced nociceptive reaction models, and their usefulness as neuropathic pain models is not disclosed.

It is an object of the present invention to provide a therapeutic agent for neuropathic pain. It is another object of the present invention to provide a neuropathic pain animal model in which the therapeutic effect of a drug against neuropathic pain can be evaluated, to provide a method for evaluating an effective compound for treating neuropathic pain using the animal model, and to provide a compound obtained by the evaluation method.

DISCLOSURE OF INVENTION

The present inventors have carried out thorough research to overcome the difficulties described above, and have discovered that a compound represented by general formula (I) alleviates neuropathic pain. It has also been discovered that an animal model which generates neuropathic pain can be produced by administering an octahydroisoquinoline derivative represented by general formula (II), and that the animal model can be used for the evaluation of a compound which alleviates neuropathic pain, and thus the present invention has been achieved.

That is, in one aspect of the present invention, a therapeutic agent for neuropathic pain contains, as an active ingredient, a compound represented by general formula (I) or a pharmacologically acceptable acid addition salt thereof:

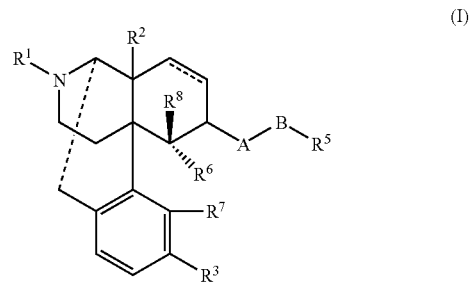

(I)

wherein $\equiv$ represents a double bond or a single bond; $R^1$ represents an alkyl group having 1 to 5 carbon atoms, a cycloalkylalkyl group having 4 to 7 carbon atoms, a cycloalkenylalkyl group having 5 to 7 carbon atoms, an aryl group having 6 to 12 carbon atoms, an aralkyl group having 7 to 13 carbon atoms, an alkenyl group having 4 to 7 carbon atoms, an allyl group, a furan-2-yl-alkyl group having 1 to 5 carbon atoms, or a thiophene-2-yl-alkyl group having 1 to 5 carbon atoms; $R^2$ represents hydrogen, a hydroxy group, a nitro group, an alkanoyloxy group having 1 to 5 carbon atoms, an alkoxy group having 1 to 5 carbon atoms, an alkyl group having 1 to 5 carbon atoms, or —$NR^9R^{10}$; $R^9$ represents hydrogen or an alkyl group having 1 to 5 carbon atoms; $R^{10}$ represents hydrogen, an alkyl group having 1 to 5 carbon atoms, or —C(=O)$R^{11}$; $R^{11}$ represents hydrogen, a phenyl group, or an alkyl group having 1 to 5 carbon atoms; $R^3$ represents hydrogen, a hydroxy group, an alkanoyloxy group having 1 to 5 carbon atoms, or an alkoxy group having 1 to 5 carbon atoms; A represents —XC(=Y)—, —XC(=Y)Z—, —X—, or —$XSO_2$— (where each of X, Y, and Z independently represents $NR^4$, S, or O; $R^4$ represents hydrogen, a straight or branched alkyl group having 1 to 5 carbon atoms, or an aryl group having 6 to 12 carbon atoms; and each $R^4$ may be identical or different); B represents a valence bond, a straight or branched alkylene group having 1 to 14 carbon atoms (which may have at least one substituent selected from the group consisting of an alkoxy group having 1 to 5 carbon atoms, an alkanoyloxy group having 1 to 5 carbon atoms, a hydroxy group, fluoro, chloro, bromo, iodo, an amino group, a nitro group, a cyano group, a trifluoromethyl group, and a phenoxy group, where one to three methylene groups may be replaced with carbonyl groups), a straight or branched acyclic unsaturated hydrocarbon containing one to three double bonds and/or triple bonds and having 2 to 14 carbon atoms (which may have at least one substituent selected from the group consisting of an alkoxy group having 1 to 5 carbon atoms, an alkanoyloxy group having 1 to 5 carbon atoms, a hydroxy group, fluoro, chloro, bromo, iodo, an amino group, a nitro group, a cyano group, a trifluoromethyl group, and a phenoxy group, where one to three methylene groups may be replaced with carbonyl groups), or a straight or branched saturated or unsaturated hydrocarbon containing one to five thioether bonds, ether bonds, and/or amino bonds and having 1 to 14 carbon atoms (where any hetero atom is not directly bonded to A, and one to three methylene groups may be replaced with carbonyl groups); $R^5$ represents hydrogen or an organic group having a basic skeleton selected from the group consisting of the following formulae:

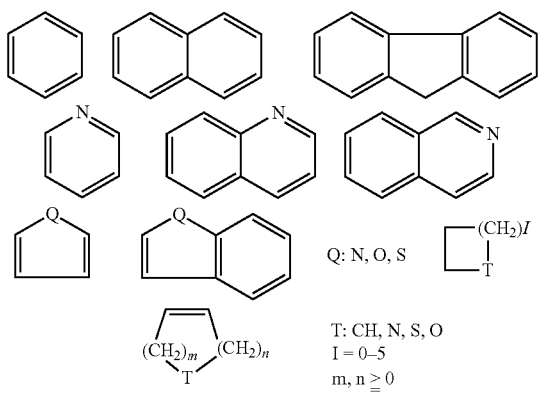

ORGANIC GROUPS REPRESENTED BY $R^5$ (where the organic group may have at least one substituent selected from the group consisting of an alkyl group having 1 to 5 carbon atoms, an alkoxy group having 1 to 5 carbon atoms, an alkanoyloxy group having 1 to 5 carbon atoms, a hydroxy group, fluoro, chloro, bromo, iodo, an amino group, a nitro group, a cyano group, an isothiocyanate group, a trifluoromethyl group, a trifluoromethoxy group, and a methylenedioxy group); $R^6$ represents hydrogen; $R^7$ represents hydrogen, a hydroxy group, an alkoxy group having 1 to 5 carbon atoms, or an alkanoyloxy group having 1 to 5 carbon atoms, or $R^6$ and $R^7$ together forming —O—, —$CH_2$—, or —S—; and $R^8$ is hydrogen, an alkyl group having 1 to 5 carbon atoms, or an alkanoyl group having 1 to 5 carbon atoms.

In another aspect of the present invention, in a neuropathic pain animal model, pain reaction is generated by administering a compound represented by general formula (II):

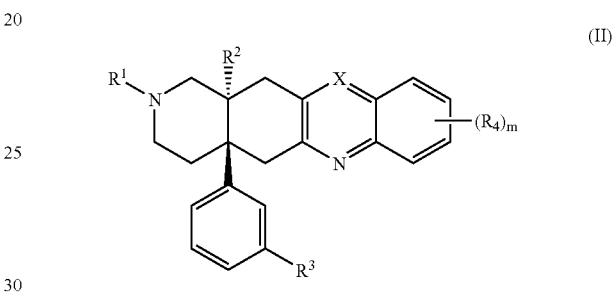

(II)

wherein $R^1$ represents hydrogen, an alkyl group having 1 to 5 carbon atoms, a cycloalkylalkyl group having 4 to 7 carbon atoms, a cycloalkenylalkyl group having 5 to 7 carbon atoms, an aralkyl group having 7 to 13 carbon atoms, an alkenyl group having 3 to 7 carbon atoms, a furan-2-yl-alkyl group (where the alkyl moiety has 1 to 5 carbon atoms), or a thiophene-2-yl-alkyl (where the alkyl moiety has 1 to 5 carbon atoms); $R^2$ represents hydrogen, a hydroxy group, an alkoxy group having 1 to 5 carbon atoms, or an alkanoyloxy group having 1 to 5 carbon atoms; $R^3$ represents hydrogen, a hydroxy group, an alkoxy group having 1 to 5 carbon atoms, an alkanoyloxy group having 1 to 5 carbon atoms, or an aralkyloxy group having 7 to 13 carbon atoms; X represents CH or N; m is an integer from 0 to 2; and each of integer m of $R^4$ is independently fluoro, chloro, bromo, iodo, an alkyl group having 1 to 5 carbon atoms, an alkoxy group having 1 to 5 carbon atoms, a nitro group, an amino group, or an alkylamino group. The present invention also relates to a method for evaluating a compound for alleviating neuropathic pain using the model, and to a compound obtained by the evaluation method.

BEST MODE FOR CARRYING OUT THE INVENTION

Figure 1:
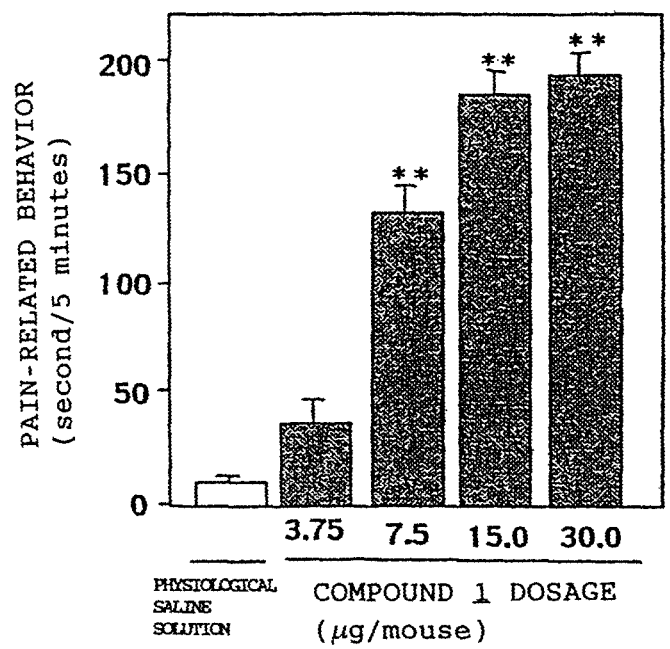
FIG. 1 is a graph which illustrates that the pain-related behavior induced by intrathecal administration of Compound 1 increases dose-dependently.

A therapeutic agent for neuropathic pain of the present invention contains, as an active ingredient, a compound represented by general formula (I) or a pharmacologically acceptable acid addition salt thereof:

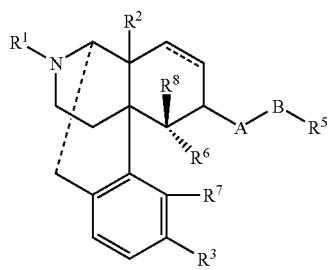

(I)

wherein ═ represents a double bond or a single bond; $R^1$ represents an alkyl group having 1 to 5 carbon atoms, a cycloalkylalkyl group having 4 to 7 carbon atoms, a cycloalkenylalkyl group having 5 to 7 carbon atoms, an aryl group having 6 to 12 carbon atoms, an aralkyl group having 7 to 13 carbon atoms, an alkenyl group having 4 to 7 carbon atoms, an allyl group, a furan-2-yl-alkyl group having 1 to 5 carbon atoms, or a thiophene-2-yl-alkyl group having 1 to 5 carbon atoms; $R^2$ represents hydrogen, a hydroxy group, a nitro group, an alkanoyloxy group having 1 to 5 carbon atoms, an alkoxy group having 1 to 5 carbon atoms, an alkyl group having 1 to 5 carbon atoms, or —$NR^9R^{10}$; $R^9$ represents hydrogen or an alkyl group having 1 to 5 carbon atoms; $R^{10}$ represents hydrogen, an alkyl group having 1 to 5 carbon atoms, or —C(═O)$R^{11}$; $R^{11}$ represents hydrogen, a phenyl group, or an alkyl group having 1 to 5 carbon atoms; $R^3$ represents hydrogen, a hydroxy group, an alkanoyloxy group having 1 to 5 carbon atoms, or an alkoxy group having 1 to 5 carbon atoms; A represents —XC(═Y)—, —XC(═Y)Z—, —X—, or —$XSO_2$— (where each of X, Y, and Z independently represents $NR^4$, S, or O; $R^4$ represents hydrogen, a straight or branched alkyl group having 1 to 5 carbon atoms, or an aryl group having 6 to 12 carbon atoms; and each $R^4$ may be identical or different); B represents a valence bond, a straight or branched alkylene group having 1 to 14 carbon atoms (which may have at least one substituent selected from the group consisting of an alkoxy group having 1 to 5 carbon atoms, an alkanoyloxy group having 1 to 5 carbon atoms, a hydroxy group, fluoro, chloro, bromo, iodo, an amino group, a nitro group, a cyano group, a trifluoromethyl group, and a phenoxy group, where one to three methylene groups may be replaced with carbonyl groups), a straight or branched acyclic unsaturated hydrocarbon containing one to three double bonds and/or triple bonds and having 2 to 14 carbon atoms (which may have at least one substituent selected from the group consisting of an alkoxy group having 1 to 5 carbon atoms, an alkanoyloxy group having 1 to 5 carbon atoms, a hydroxy group, fluoro, chloro, bromo, iodo, an amino group, a nitro group, a cyano group, a trifluoromethyl group, and a phenoxy group, where one to three methylene groups may be replaced with carbonyl groups), or a straight or branched saturated or unsaturated hydrocarbon containing one to five thioether bonds, ether bonds, and/or amino bonds and having 1 to 14 carbon atoms (where any hetero atom is not directly bonded to A, and one to three methylene groups may be replaced with carbonyl groups); $R^5$ represents hydrogen or an organic group having a basic skeleton selected from the group consisting of the following formulae:

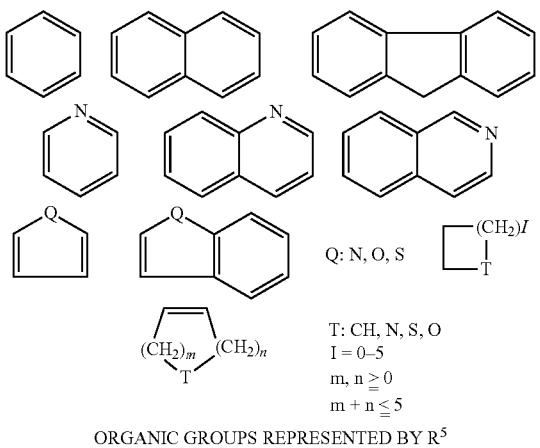

ORGANIC GROUPS REPRESENTED BY $R^5$ (where the organic group may have at least one substituent selected from the group consisting of an alkyl group having 1 to 5 carbon atoms, an alkoxy group having 1 to 5 carbon atoms, an alkanoyloxy group having 1 to 5 carbon atoms, a hydroxy group, fluoro, chloro, bromo, iodo, an amino group, a nitro, group, a cyano group, an isothiocyanate group, a trifluoromethyl group, a trifluoromethoxy group, and a methylenedioxy group); $R^6$ represents hydrogen; $R^7$ represents hydrogen, a hydroxy group, an alkoxy group having 1 to 5 carbon atoms, or an alkanoyloxy group having 1 to 5 carbon atoms, or $R^6$ and $R^7$ together forming —O—, —$CH_2$—, or —S—; and $R^8$ represents hydrogen, an alkyl group having 1 to 5 carbon atoms, or an alkanoyl group having 1 to 5 carbon atoms.

In the compound represented by general formula (I), preferable examples of $R^1$ include an alkyl group having 1 to 5 carbon atoms, a cycloalkylmethyl group having 4 to 7 carbon atoms, a cycloalkenylmethyl group having 5 to 7 carbon atoms, a phenylalkyl group having 7 to 13 carbon atoms, an alkenyl group having 4 to 7 carbon atoms, an allyl group, a furan-2-yl-alkyl group having 1 to 5 carbon atoms, and a thiophene-2-yl-alkyl group having 1 to 5 carbon atoms, and more preferable examples of $R^1$ include methyl, ethyl, propyl, butyl, isobutyl, cyclopropylmethyl, allyl, benzyl, phenethyl, furan-2-yl-methyl, and thiophene-2-yl-methyl groups.

Preferable examples of $R^2$ include hydrogen and hydroxy, nitro, acetoxy, methoxy, methyl, ethyl, propyl, amino, dimethylamino, acetylamino, and benzoylamino groups, and more preferable examples of $R^2$ include hydrogen and hydroxy, nitro, acetoxy, methyl, and dimethylamino groups.

Preferable examples of $R^3$ include hydrogen and hydroxy, acetoxy, and methoxy groups, and more preferable examples of $R^3$ include hydroxy, acetoxy, and methoxy groups.

Preferable examples of A include —$NR^4C(=O)$—, —$NR^4C(=S)$—, —$NR^4C(=O)O$—, —$NR^4C(=O)NR^4$—, —$NR^4C(=S)NR^4$—, —$NR^4C(=O)S$—, —$OC(=O)$—, $OC(=O)O$—, —$SC(=O)$—, —$NR^4$—, —O—, —$NR^4SO_2$—, and $OSO_2$—, and more preferable examples of A include —$NR^4C(=O)$—, —$NR^4C(=S)$—, —$NR^4C(=O)O$—, —$NR^4C(=O)NR^4$—, —$NR^4C(=S)NR^4$—, and —$NR^4SO_2$—.

Preferable examples of $R^4$ include hydrogen and straight or branched alkyl groups having 1 to 5 carbon atoms, and more preferable examples of $R^4$ include a straight or branched alkyl group having 1 to 5 carbon atoms, and particularly, methyl, ethyl, propyl, butyl, and isobutyl groups. Among them, —$XC(=Y)$— (where X represents $NR^4$, S, or O; Y represents O; and $R^4$ represents hydrogen or an alkyl group having 1 to 5 carbon atoms), —$XC(=Y)Z$—, —X—, or —$XSO_2$— (where X represents $NR^4$; Y represents O or S; Z represents $NR^4$ or O; and $R^4$ represents hydrogen or an alkyl group having 1 to 5 carbon atoms) is preferred, and —$XC(=Y)$— or —$XC(=Y)Z$— (where X represents $NR^4$; Y represents O; and $R^4$ represents an alkyl group having 1 to 5 carbon atoms) is more preferred.

Preferable examples of B include —$(CH_2)_n$— (n=0 to 10), —$(CH_2)_n$—$C(=O)$— (n=1 to 4), —$CH=CH$—$(CH_2)_n$— (n=0 to 4), —$C\equiv C$—$(CH_2)_n$— (n=0 to 4), —$CH_2$—O—, —$CH_2$—S—, —$(CH_2)_2$—O—$CH_2$—, and —$CH=CH$—$CH=CH$—$(CH_2)_n$— (n=0 to 4), and more preferable examples of B include —$(CH_2)_n$— (n=1 to 3), —$CH=CH$—$(CH_2)_n$— (n=0 to 4), —$CeC$—$(CH_2)_n$— (n=0 to 4), —$CH_2$—O—, and —$CH_2$—S—. Among them, a linear alkylene group having 1 to 6 carbon atoms, —$CH=CH$—$(CH_2)_n$— (n=0 to 4), —$CH=CH$—, —$C\equiv C$—, —$CH_2$—O—, or —$CH_2$—S— is most preferable. Particularly, —$CH=CH$— or —$C\equiv C$— is desirable. (Of course, the preferable examples include the groups which have various substituents described above.)

Preferable examples of $R^5$ include hydrogen and organic groups having the following basic skeletons:

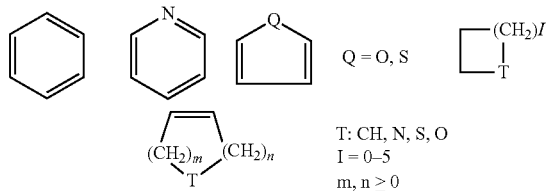

ORGANIC GROUPS REPRESENTED BY $R^5$ (where the organic group may have at least one substituent selected from the group consisting of an alkyl group having 1 to 5 carbon atoms, an alkoxy group having 1 to 5 carbon atoms, an alkanoyloxy group having 1 to 5 carbon atoms, a hydroxy group, fluoro, chloro, bromo, iodo, an amino group, a nitro group, a cyano group, an isothiocyanate group, a trifluoromethyl group, a trifluoromethoxy group, and a methylenedioxy group). Among them, more preferred are hydrogen and organic groups having the following basic skeletons:

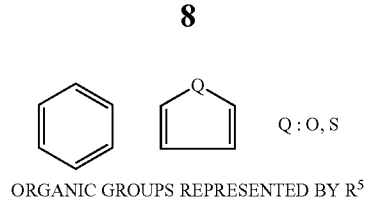

ORGANIC GROUPS REPRESENTED BY $R^5$ (where the organic group may have at least one substituent selected from the group consisting of an alkyl group having 1 to 5 carbon atoms, an alkoxy group having 1 to 5 carbon atoms, an alkanoyloxy group having 1 to 5 carbon atoms, a hydroxy group, fluoro, chloro, bromo, iodo, an amino group, a nitro group, a cyano group, an isothiocyanate group, a trifluoromethyl group, a trifluoromethoxy group, and a methylenedioxy group). More specifically, preferable examples include, but are not limited to, hydrogen and phenyl, 4-methylphenyl, 3-methylphenyl, 2-methylphenyl, 3,4-dimethylphenyl, 3,5-dimethylphenyl, 4-methoxyphenyl, 3-methoxyphenyl, 2-methoxyphenyl, 3,4-dimethoxyphenyl, 4-hydroxyphenyl, 3-hydroxyphenyl, 3,4-dihydroxyphenyl, 4-fluorophenyl, 3-fluorophenyl, 2-fluorophenyl, 3,4-difluorophenyl, perfluorophenyl, 4-chlorophenyl, 3-chlorophenyl, 2-chlorophenyl, 3,4-dichlorophenyl, 2,4-dichlorophenyl, 2,4,5-trichlorophenyl, 2,4,6-trichlorophenyl, 4-bromophenyl, 3-bromophenyl, 2-bromophenyl, 4-nitrophenyl, 3-nitrophenyl, 2-nitrophenyl, 4-aminophenyl, 3-aminophenyl, 2-aminophenyl, 4-trifluoromethylphenyl, 3-trifluoromethylphenyl, 2-trifluoromethylphenyl, 4-trifluoromethoxyphenyl, 3-trifluoromethoxyphenyl, 2-trifluoromethoxyphenyl, 3,4 methylenedioxyphenyl, 3-furanyl, 2-furanyl, 3-thienyl, 2-thienyl, cyclopentyl, and cyclohexyl groups.

In the compound represented by general formula (I), preferably, $R^1$ is an alkyl group having 1 to 5 carbon atoms, a cycloalkylmethyl group having 4 to 7 carbon atoms, a cycloalkenylmethyl group having 5 to 7 carbon atoms, a phenylalkyl group having 7 to 13 carbon atoms, an alkenyl group having 4 to 7 carbon atoms, an allyl group, a furan-2-ylalkyl group having 1 to 5 carbon atoms, or a thiophene-2-yl-alkyl group having 1 to 5 carbon atoms; $R^2$ is hydrogen, a hydroxy group, an alkanoyloxy group having 1 to 5 carbon atoms, or an alkoxy group having 1 to 5 carbon atoms; $R^3$ is hydrogen, a hydroxy group, an alkanoyloxy group having 1 to 5 carbon atoms, or an alkoxy group having 1 to 5 carbon atoms; A is —$XC(=Y)$— (where X represents $NR^4$, S, or O; Y represents O; and $R^4$ represents hydrogen or an alkyl group having 1 to 5 carbon atoms), —$XC(=Y)Z$—, —X—, or —$XSO_2$— (where X represents $NR^4$; Y represents O or S; Z represents $NR^4$ or O; and $R^4$ represents hydrogen or an alkyl group having 1 to 5 carbon atoms); B is —$(CH_2)_n$— (n=0 to 10), —$(CH_2)_n$—$C(=O)$—(n=1 to 4), —$CH=CH$—$(CH_2)_n$— (n=0 to 4), —$C\equiv C$—$(CH_2)_n$— (n=0 to 4), —$CH_2$—O—, —$CH_2$—S—, —$(CH_2)_2$—O—$CH_2$—, or —$CH=CH$—$CH=CH$—$(CH_2)_n$— (n=0 to 4); $R^5$ is hydrogen or an organic group having a basic skeleton selected from the group consisting of the following formulae:

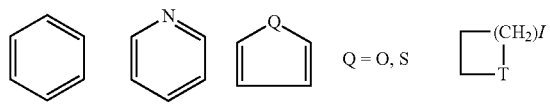

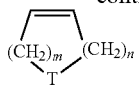

T: CH, N, S, O
I = 0–5
m, n ≥ 0
m + n ≤ 5

ORGANIC GROUPS REPRESENTED BY $R^5$ (where the organic group may have at least one substituent selected from the group consisting of an alkyl group having 1 to 5 carbon atoms, an alkoxy group having 1 to 5 carbon atoms, an alkanoyloxy group having 1 to 5 carbon atoms, a hydroxy group, fluoro, chloro, bromo, iodo, an amino group, a nitro group, a cyano group, an isothiocyanate group, a trifluoromethyl group, a trifluoromethoxy group, and a methylenedioxy group); $R^6$ and $R^7$ together form —O—; and $R^8$ is hydrogen.

In the compound represented by general formula (I), more preferably, $R^1$ is a methyl, ethyl, propyl, butyl, isobutyl, cyclopropylmethyl, allyl, benzyl, phenethyl, furan-2-yl-methyl, or thiophene-2-yl-methyl group; $R^2$ is hydrogen, a hydroxy group, or an acetoxy group; $R^3$ is a hydroxy, acetoxy, or methoxy group; A is —XC(=Y)— or —XC(=Y)Z— (where X represents $NR^4$; Y represents O; and $R^4$ represents an alkyl group having 1 to 5 carbon atoms); B is —$(CH_2)_n$— (n=1 to 3), —CH=CH—$(CH_2)_n$— (n=0 to 4), —C≡C—$(CH_2)_n$— (n=0 to 4), —$CH_2$—O—, or —$CH_2$—S—; $R^5$ is hydrogen or an organic group having a basic skeleton selected from the group consisting of the following formulae:

   Q: O, S

ORGANIC GROUPS REPRESENTED BY $R^5$ (where the organic group may have at least one substituent selected from the group consisting of an alkyl group having 1 to 5 carbon atoms, an alkoxy group having 1 to 5 carbon atoms, an alkanoyloxy group having 1 to 5 carbon atoms, a hydroxy group, fluoro, chloro, bromo, iodo, an amino group, a nitro group, a cyano group, an isothiocyanate group, a trifluoromethyl group, a trifluoromethoxy group, and a methylenedioxy group); $R^6$ and $R^7$ together form —O—; and $R^8$ is hydrogen.

The morphinan derivatives represented by general formula (I) may be produced by the method disclosed in Japanese Patent No. 2525552.

Preferable examples of pharmacologically acceptable acid addition salts include, but are not limited to, inorganic salts such as hydrochlorides, sulfates, nitrates, hydrobromides, hydroiodides, and phosphates; organic carboxylates such as acetates, lactates, citrates, oxalates, glutarates, malates, tartrates, fumarates, mandelates, maleates, benzoates, and phtalates; and organic sulfonates such as methanesulfonates, ethanesulfonates, benzenesulfonates, p-toluenesulfonates, and camphorsulfonates. More preferable examples include hydrochlorides, hydrobromides, phosphates, tartrates, maleates, and methanesulfonates.

Since the compounds represented by the general formula (I) or the pharmacologically acceptable salts thereof alleviate neuropathic pain in which sufficient therapeutic effects are not achieved by morphine, which is widely used as an analgesic, it has become clear that they are effective as therapeutic agents for neuropathic pain.

When the compounds represented by the general formula (I) are used as therapeutic agents for neuropathic pain, the compounds can be used alone or in combination with other compounds represented by the general formula (I) as active ingredients. After the compounds are purified and pass the necessary stability test, the compounds can be orally or parenterally administered as they are, or as pharmaceutical compositions mixed with known, pharmacologically acceptable acids, carrier, excipients, etc. Examples of administration modes include injections, orally administered drugs, such as tablets, capsules, granules, powdered drugs, and syrups, and administration per rectum by suppositories. The content of the active ingredient in the therapeutic agent for neuropathic pain of the present invention is preferably 1 to 90% by weight, and more preferably, 30 to 70% by weight. Although the dosage is appropriately selected depending on the symptoms, age, body weight, administration modes, etc., the dose per day for an adult is 0.001 mg to 1 g in the case of injections, and 0.005 mg to 10 g in the case of orally administered drugs, and administration can be performed once or several times a day. Additionally, various adjuvants may be mixed therewith in order to improve the therapeutic effects on neuropathic pain. Furthermore, the therapeutic agents of the present invention may be combined with known drugs used for treating pain. Examples of drugs which can be combined with the therapeutic agent include, but are not particularly limited to, antidepressants, antianxiety agents, anticonvulsants, topical anesthetics, sympathetic agents, NMDA-receptor antagonists, calcium channel blockers, serotonin receptor antagonists, GABA-receptor activators, opioid agonists, and anti-inflammatory agents. More specifically, the examples are amitriptyline, imipramine, desipramine, fluoxetine, carbamazepine, diazepam, gabepentin, valproic acid, lidocaine, clonidine, phentolamine, prazosin, ketamine, ifenprodil, dextromethorphan, mexiletine, ketanserin, sarpogrelate hydrochloride, benzodiazepine, barbiturate, tramadol, fentanyl, and dicrofenac. Furthermore, in the case of treatment for neuropathic pain caused by virus infection, antiviral agents, such as acyclovir and famciclovir, can be combined with the therapeutic agent of the present invention. In addition, nerve block therapy, acupuncture, actinotherapy, epidural electrostimulation therapy, etc. that are used for treatment of neuropathic pain can be combined with the therapeutic agent of the present invention.

From the viewpoint of the causes of pain, neuropathic pain to be treated includes pain developing when damage and dysfunction occur in the nervous system itself due to external injuries, surgery, radiation therapy or drug therapy, and also due to diabetes, alcoholic and other drug poisoning, amyloidosis, virus infection, etc., without stimuli to nociceptors due to tissue damage. From the viewpoint of the locations of the nerves in which dysfunction occurs, examples of neuropathic pain include trigeminal neuralgia, glossopharyngeal neuralgia, causalgia (a pain syndrome in which vascular nerve disorders and dyshidrosis occur due to sympathetic nerve dysfunction where there has been partial damage to the peripheral nerves of limbs or the large branches thereof, and persistent, burning pain and nutritional disorders of tissues are observed), reflex sympathetic dystrophy, deafferentation pain, and thalamic pain. Other examples are herpetic pain, postherpetic neuralgia, tonic spasm pain, erythermalgia, poliomyelitis pain, phantom limb pain, pain in AIDS-infected patients, multiple sclerosis pain, and pain associated with the Parkinsonian syndrome. In particular, the therapeutic agent of the present invention is effective in treating pain associated with zosteriform skin lesions, for example, herpetic pain and postherpetic neuralgia.

The present invention also relates to an animal model in which pain reaction is generated by administering a compound represented by general formula (II) to the animal, to a method for evaluating a compound for alleviating neuropathic pain using the model, and to a compound obtained by the evaluation method:

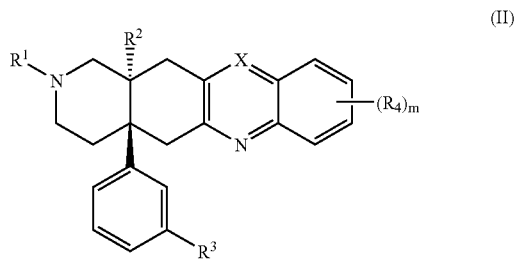

(II)

wherein $R^1$ represents hydrogen, an alkyl group having 1 to 5 carbon atoms, a cycloalkylalkyl group having 4 to 7 carbon atoms, a cycloalkenylalkyl group having 5 to 7 carbon atoms, an aralkyl group having 7 to 13 carbon atoms, an alkenyl group having 3 to 7 carbon atoms, a furan-2-yl-alkyl group (where the alkyl moiety has 1 to 5 carbon atoms), or a thiophene-2-yl-alkyl (where the alkyl moiety has 1 to 5 carbon atoms); $R^2$ represents hydrogen, a hydroxy group, an alkoxy group having 1 to 5 carbon atoms, or an alkanoyloxy group having 1 to 5 carbon atoms; $R^3$ represents hydrogen, a hydroxy group, an alkoxy group having 1 to 5 carbon atoms, an alkanoyloxy group having 1 to 5 carbon atoms, or an aralkyloxy group having 7 to 13 carbon atoms; X represents CH or N; m is an integer from 0 to 2; and each of integer m of $R^4$ is independently fluoro, chloro, bromo, iodo, an alkyl group having 1 to 5 carbon atoms, an alkoxy group having 1 to 5 carbon atoms, a nitro group, an amino group, or an alkylamino group.

In the compound, which is sued for making the animal model, represented by general formula (II), preferably, $R^1$ is hydrogen, an alkyl group having 1 to 5 carbon atoms, a cycloalkylmethyl group having 4 to 7 carbon atoms, a cycloalkenylmethyl group having 5 to 7 carbon atoms, a phenyl group, a naphthyl group, a phenylaralkyl group having 7 to 13 carbon atoms, an alkenyl group having 3 to 7 carbon atoms, a furan-2-yl-alkyl group (where the alkyl moiety has 1 to 5 carbon atoms), or a thiophene-2-yl-alkyl group (where the alkyl moiety has 1 to 5 carbon atoms); $R^2$ is hydrogen, a hydroxyl group, an acetoxy group, a propionyloxy group, a methoxy group, or an ethoxy group; $R^3$ is hydrogen, a hydroxyl group, an acetoxy group, a propionyloxy group, a methoxy group, and ethoxy group, or a benzyloxy group; X is CH; m is an integer from 0 to 2; and $R^4$ is independently fluoro, chloro, bromo, an alkyl group having 1 to 5 carbon atoms, an alkoxy group having 1 to 5 carbon atoms, a nitro group, or an amino group. More preferably, $R^1$ is hydrogen, a methyl group, an ethyl group, a cyclopropylmethyl group, a cyclobutylmethyl group, a cyclopentylmethyl group, a cyclopentenylmethyl group, a cyclohexenylmethyl group, a benzyl group, a phenethyl group, a trans-2-butenyl group, a 3-methyl-2-butenyl group, an allyl group, a furan-2-yl-methyl group, or a thiophene-2-yl-methyl group, $R^2$ is hydrogen, a hydroxyl group, an acetoxy group, or a methoxy group; $R^3$ is hydrogen, a hydroxyl group, an acetoxy group, a methoxy group, or a benzyloxy group; X is CH; m is an integer from 0 to 2; an integer m of $R^4$ is independently fluoro, chloro, bromo, a methyl group, a methoxy group, a nitro group, or an amino group.

General formula (II) shows a relative configuration of the compound, and examples of the compound of the present invention include racemic modifications, and optical isomers of which absolute structures are represented by general formulae (A) and (B) below. The optical isomers of which structures are represented by general formula (A) are preferable.

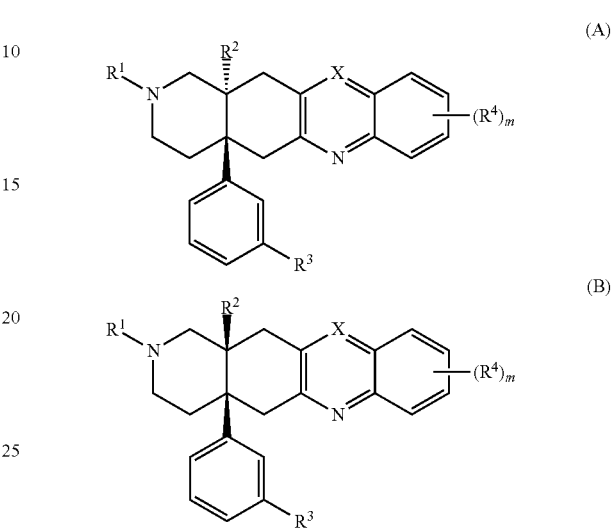

(A)

(B)

More preferable is (+)-4a-(3-hydroxyphenyl)-2-methyl-1,2,3,4,4a,5,12,12a-octohydro-trans-quinolino[2,3-g]isoquinoline of which the formula is shown below.

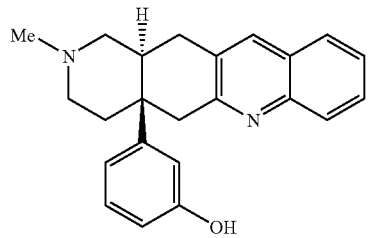 [SMILES: CN1CC[C@@]2(c3cccc(O)c3)Cc3nc4ccccc4cc3C[C@@H]2C1]

The animal used in the present invention is not particularly limited, but is preferably a rodent and more preferably a mouse. The compound to generate neuropathic pain is preferably administered intrathecally. When a mouse is used, although the strain, age in weeks, sex, etc., of the mouse are not particularly limited, as the age in weeks increases, that is, as the body weight increases, intrathecal administration to the animal becomes more difficult. Therefore, a mouse with a body weight of 25 to 35 g is preferably used.

In order to induce neuropathic pain in a mouse, desirably, the compound represented by general formula (II) is intrathecally administered in an amount of approximately 5 to 30 μg, and usually, approximately 15 μg is preferably used. As the solvent for administration, an isotonic solution is preferably used, and an ordinary physiological saline solution can be used sufficiently. The intrathecal dosage is preferably in the range of several to 20 μl, and more preferably approximately 5 μl. When intrathecal administration is performed, an injection needle of 25 to 30 gauges is preferably used.

In the evaluation method of the present invention, various types of indexes for animal behavioral response can be used. Preferably, scratching, biting, and licking behavior and the like which are not often observed in normal animals are used as indexes. In order to make evaluations by observing such behavior, the animals may be directly observed. Alternatively, evaluations may be made using recording media such as videos, or using machines which detect the movements of animals based on heat emitted by the animals, or the like. With respect to the evaluation time, the period in which the behavior is stably developed after the administration of the compound represented by general formula (II) is desirable, and in particular, evaluation is preferably made for 5 minutes from 5 minutes after administration.

When screening or evaluation of a drug for treating neuropathic pain is made using the animal model of the present invention, the administration route of the drug to be evaluated, solvent, dosage, etc., are not particularly limited, and they can be appropriately selected in consideration of the characteristics of the drug itself.

By the evaluation method described above, a compound which inhibits the behavior of the animal, for example, scratching, biting, and licking, can be obtained as a compound which alleviates neuropathic pain.

Since the compound thus obtained demonstrates effectiveness in other neuropathic pain animal models, the animal model is proved to be useful. Accordingly, it is possible to evaluate a compound, and a compound which demonstrates effectiveness can be developed as a therapeutic agent for neuropathic pain. Therefore, the animal model, the evaluation method using the animal model, screening or evaluation of the drug, and the compound obtained by the evaluation described above lead to great progress in the development of drugs for treating neuropathic pain.

The present invention will be described in detail based on the examples below.

EXAMPLES

Example 1

Production of the Neuropathic Pain Animal Model

Mice (ddY; weighing 22 to 25 g when the experiment was started) were kept in a plastic cage at a constant temperature and humidity (22±1° C., 55±5%) under a 12-hour light-dark cycle. The mice had free access to food and water.

(+)-4a-(3-hydroxyphenyl)-2-methyl-1,2,3,4,4a,5,12,12a-octahydrotrans-quinolino[2,3-g]isoquinoline (Compound 1) was dissolved in a physiological saline solution (Ohtsuka Pharmaceutical Co., Ltd.) and was intrathecally administered to the mice without anesthetization. The intrathecal dose of the drug solution per mouse was 4 µl, and a 30 gauge needle and a 25 µl Hamilton syringe were used according to the method disclosed by Hylden and Wilcox (J. L. K. Hylden & G. L. Wilcox, Eur. J. Pharmacol., 67: 313-316, 1980).

Figure 2:
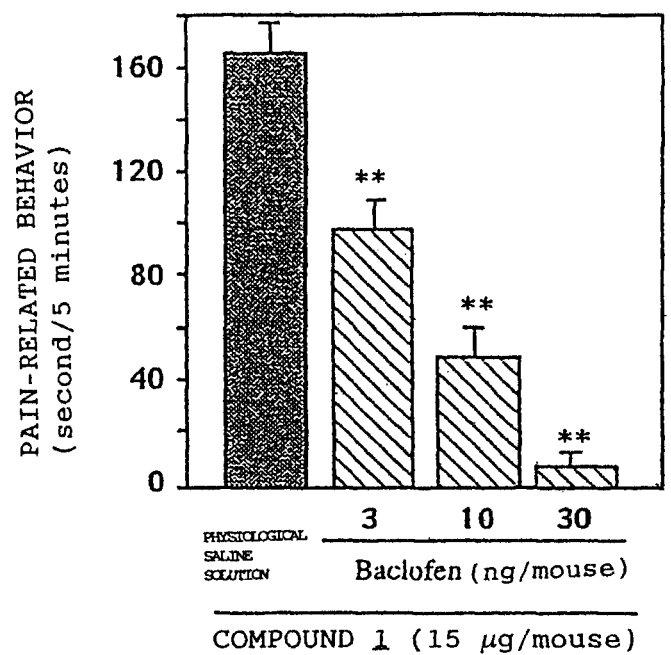
FIG. 2 is a graph showing the effect of Baclofen, a $GABA_B$-receptor agonist, on the pain-related behavior induced by intrathecal administration of Compound 1.
Figure 3:
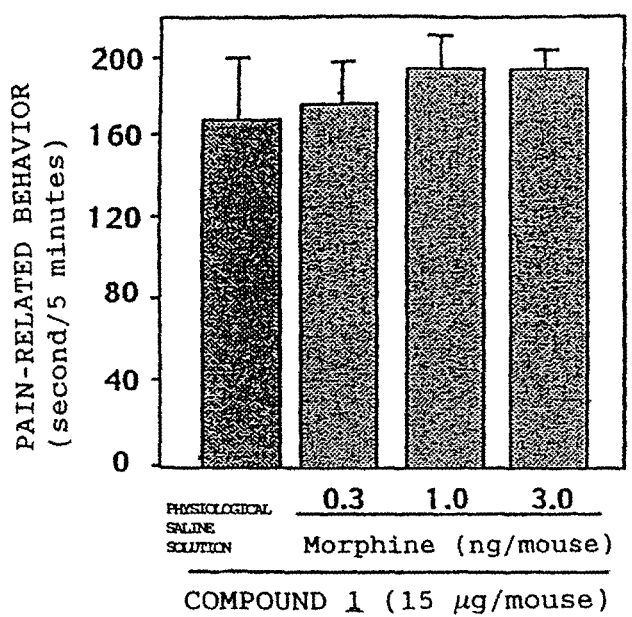
FIG. 3 is a graph showing the effect of morphine on the pain-related behavior induced by intrathecal administration of Compound 1.

Scratching, biting, and licking behavior was regarded as an index of tentative responses for nociception, and the duration of such behavior was measured for 5 minutes from 5 minutes after the administration of Compound 1 in a transparent acrylic cage (20×13×10 cm) in a single-blind manner. The results thereof are shown in FIG. 1. When Compound 1 was administered in an amount of 7.5 µg/mouse or more, the tentative responses for nociception increased significantly and dose-dependently. As shown in FIG. 2, the tentative responses for nociception induced by 15 µg/mouse of Compound 1 were inhibited dose-dependently by simultaneous intrathecal administration of Baclofen, a $GABA_B$-receptor agonist. However, as shown in FIG. 3, when morphine was intrathecally administered to mice simultaneously with Compound 1, the tentative responses for nociception induced by 15 µg/mouse of Compound 1 were not inhibited at all.

Baclofen is currently clinically used as a therapeutic agent for convulsion/paralysis due to cerebral vascular disorders and multiple sclerosis, and in animal experiments, it is known that an antinociceptive action is produced by systemic administration, intraventricular administration, and intrathecal administration. Furthermore, neuropathic pain is inhibited by the intrathecal administration of Baclofen, and the application thereof as a therapeutic agent for neuropathic pain is expected clinically. Morphine does not demonstrate effectiveness against neuropathic pain clinically. Consequently, it has become clear that the animal model of the present invention produced by intrathecally administering Compound 1 has characteristics of neuropathic pain.

Example 2

Evaluation of the Action of Inhibiting Neuropathic Pain

1

Mice (ddY; weighing 22 to 25 g when the experiment was started) were kept in a plastic cage at a constant temperature and humidity (22±1° C., 55±5%) under a 12-hour light-dark cycle. The mice had free access to food and water.

Compound 1 was dissolved in a physiological saline solution (Ohtsuka Pharmaceutical Co., Ltd.) and was intrathecally administered to the mice without anesthetization. The intrathecal dose of the drug solution per mouse was 4 µl, and a 30 gauge needle and a 25 µl Hamilton syringe were used according to the method disclosed by Hylden and Wilcox (J. L. K. Hylden & G. L. Wilcox, Eur. J. Pharmacol., 67: 313-316, 1980).

(−)-17cyclopropylmethyl-3,14β-dihydroxy-4,5α-epoxy-6β-[N-methyl-trans-3-(3-furyl)acrylamideo]morphinan hydrochloride (Compound 2) (H. Nagase et al. Chem. Pharm. Bull. 46, 366, 1998), of which the formula is shown below,

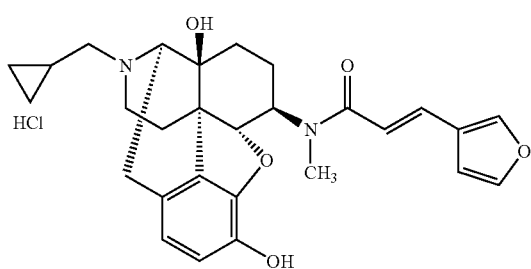

Figure 4:
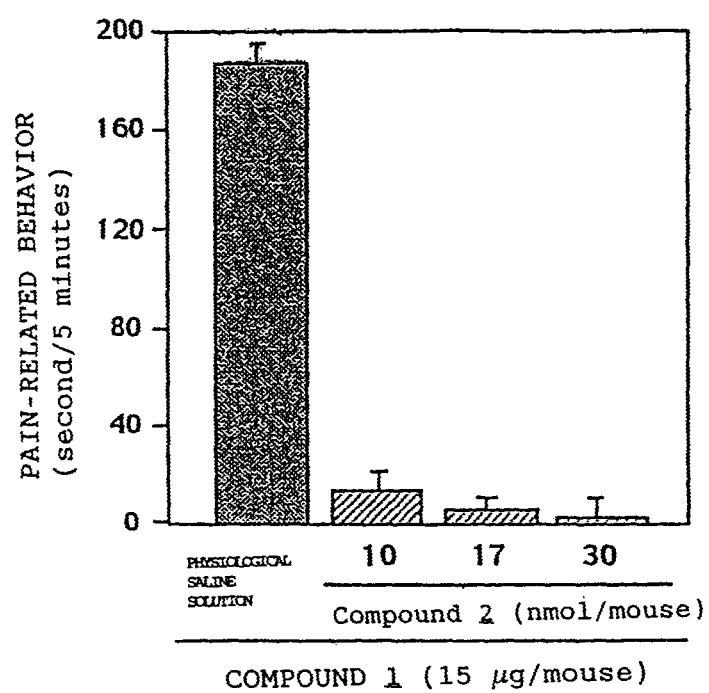
FIG. 4 is a graph showing the effect of Compound 2 on the pain-related behavior induced by intrathecal administration of Compound 1.

2 as a selective opioid κ-receptor agonist compound, was intrathecally administered to the mice simultaneously with Compound 1, and the effect thereof on neuropathic pain was evaluated based on tentative responses for nociception, such as scratching, biting, and licking behavior, as indexes. The duration of such behavior was measured for 5 minutes from 5 minutes after the administration of the simultaneous administration of Compound 2 and Compound 1 (15 µg/mouse) in a transparent acrylic cage (20×13×10 cm) in a single-blind manner. Additionally, Compound 2 was dissolved in a physiological saline solution for use. The results thereof are shown in FIG. 4. As is obvious from the graph, Compound 2 at 10 nmol/mouse significantly inhibited the tentative responses for nociception compared to the physiological saline solution-treated group, thus exhibiting effectiveness for neuropathic pain.

Example 3

Evaluation of the Action of Inhibiting Neuropathic Pain

2

Figure 5:
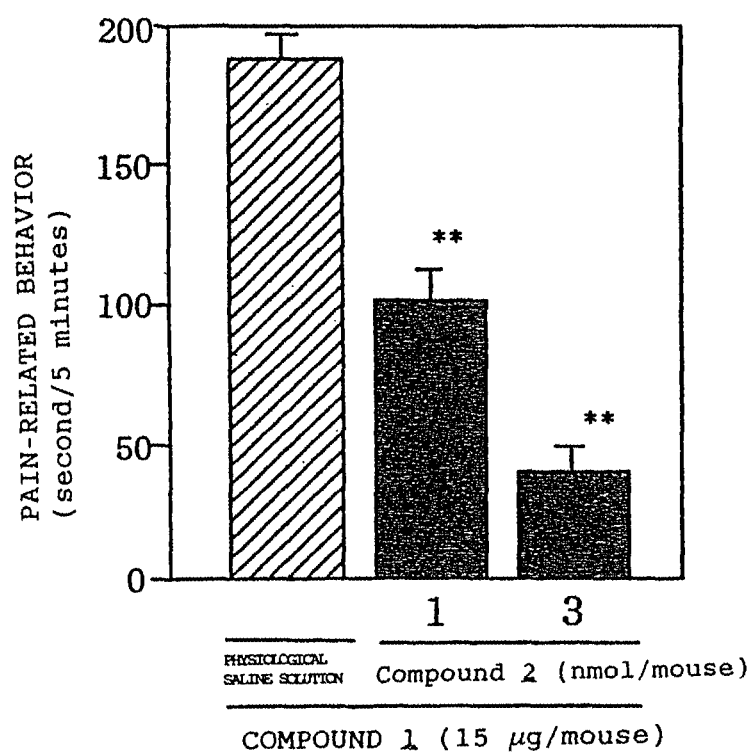
FIG. 5 is a graph showing the dose-dependent inhibitory action of Compound 2 on the pain-related behavior induced by intrathecal administration of Compound 1.
Figure 6:
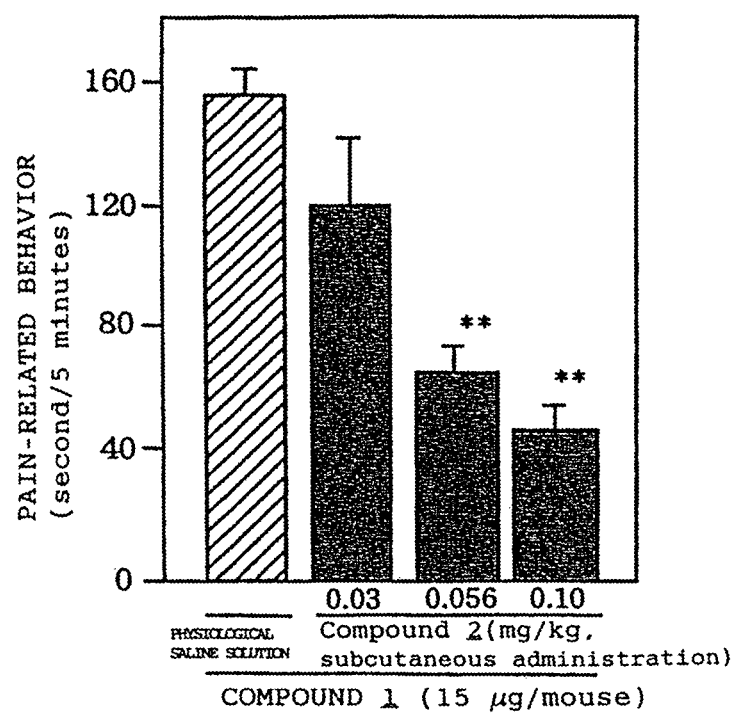
FIG. 6 is a graph showing the dose-dependent inhibitory action of Compound 2 when subcutaneously administered on the pain-related behavior induced by intrathecal administration of Compound 1.

In order to determine the effect of the drug on neuropathic pain, tentative responses for nociception were tested in the case in which a low dose of 1 or 3 nmol/mouse of Compound 2 was intrathecally administered simultaneously with Compound 1 in a manner similar to that of Example 2 and in the case in which Compound 2 was subcutaneously administered so that systemic exposure to the drug was evaluated. The results thereof are shown in FIGS. 5 and 6. In either case, it was demonstrated that the tentative responses for nociception are dose-dependently inhibited and Compound 2 is effective against neuropathic pain. Since the effectiveness of Compound 2 has also been shown in systemic exposure, it has become clear that Compound 2 is effective even if the drug is not administered topically, that is, even if the drug is administered in various dosage forms which are pharmacologically acceptable.

Example 4

Figure 7:
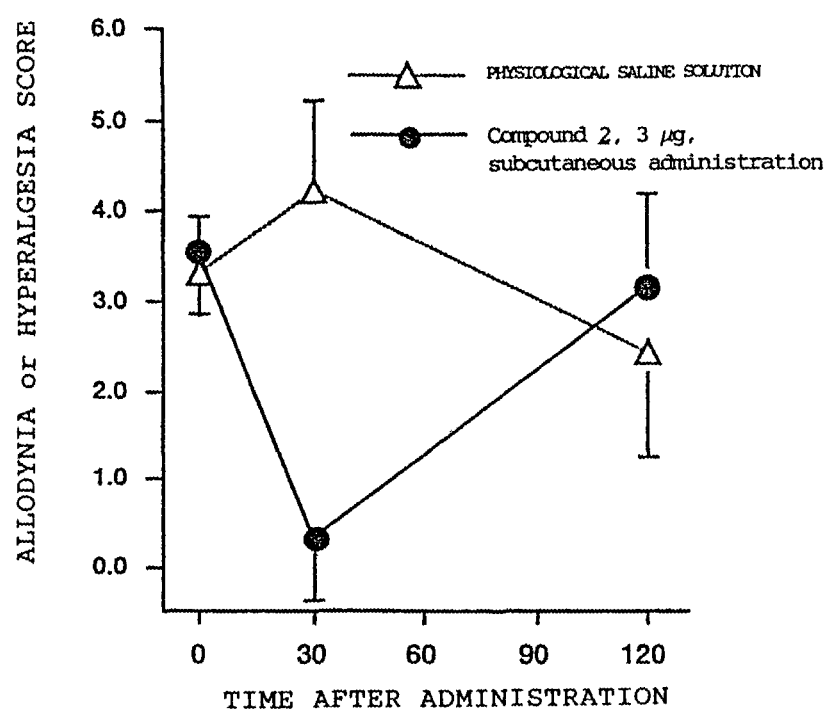
FIG. 7 is a graph showing the action of Compound 2 in inhibiting allodynia and hyperalgesia in sciatic nerve ligation models.

Evaluation of the Action of the Drug in Inhibiting Neuropathic Pain in a Sciatic Nerve Ligation Model The action of Compound 2 in inhibiting neuropathic pain was investigated using another, widely known neuropathic pain model. That is, the action of Compound 2 in a sciatic nerve ligation mouse model was investigated using a method in which the method disclosed by A. B. Malmberg and A. I. Basbaum (Pain, 76, 215-222, 1998) et al. was slightly modified. In order to measure allodynia or hyperalgesia generally observed in neuropathic pain, two von Frey hairs (0.17 and 1.48 g) having different strengths were used. Four weeks following the surgery, the mice were placed in an acrylic cage (90×100×300 mm) and allowed to acclimate for a minimum of 30 minutes. The von Frey hairs were applied perpendicularly to the soles of the hind feet so as to cause slight bending for a duration of approximately 3 seconds. This was repeated 6 times at intervals of several seconds. The reaction of the mouse was given a score in the manner described below.
  0: No reaction
  1: Lifting of hind foot
  2: Immediate escape reaction and flinching of hind paw The reactions of the surgically operated foot and the opposite foot as control were measured before the administration of the drug, and 30 minutes and 2 hours after the administration of the drug. The difference between the score of the surgically operated foot and the score of the control foot was evaluated as allodynia or hyperalgesia. That is, the larger difference indicates the larger degree of allodynia or hyperalgesia. Compound 2 was dissolved in a physiological saline solution and the drug solution was subcutaneously administered. Additionally, a physiological saline solution was used as a control solvent. The results thereof are shown in FIG. 7. Before the administration of the drug, in both groups, allodynia or hyperalgesia symptoms were shown and each difference between the score of the surgically operated foot and the score of the control foot was same. Thirty minutes after the administration, Compound 2 inhibited allodynia or hyperalgesia while the control-solvent-administered group did not show the improvement effect. After 2 hours, the effect of the drug disappeared. From the results described above, it was found that the compound which showed effectiveness in the neuropathic pain model in Example 1 also shows effectiveness in another neuropathic pain model.

Example 5

Figure 8:
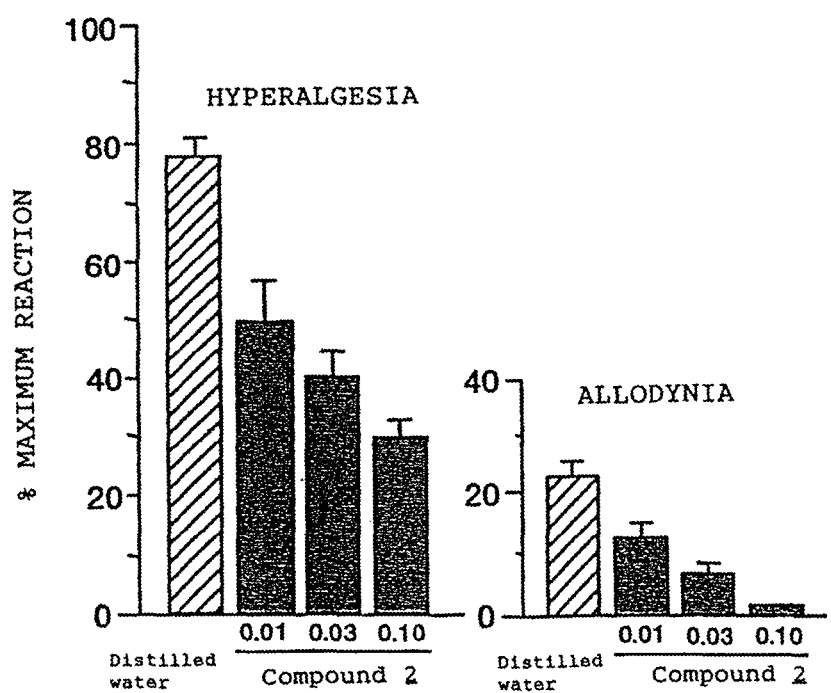
FIG. 8 is a graph showing the action of Compound 2 in inhibiting allodynia and hyperalgesia in herpetic pain models.

Evaluation of the Action of the Drug in Inhibiting Hyperalgesia and Allodynia in Pain Associated with Zosteriform Skin Lesions The therapeutic effect of Compound 2 on pain associated with zoster classified under neuropathic pain was investigated. The evaluation of the therapeutic effect was made using an animal model produced according to a method disclosed in Pain, 86, 95-101, 2000. The results when Compound 2 was orally administered are shown in FIG. 8. Thirty minutes after the administration, Compound 2 dose-dependently inhibited allodynia or hyperalgesia associated with zosteriform skin lesions, and thus it was found that Compound 2 shows effectiveness against pain associated with zoster.

The examples described above have proved that when a compound is evaluated using the animal model in Example 1, a compound which shows effectiveness has an effect of improving allodynia or hyperalgesia in another neuropathic pain animal model. Consequently, it has been confirmed that the animal model in Example 1 and the evaluation method of a compound using the model are effective, and it has also become possible to develop a compound which shows effectiveness as a therapeutic agent for neuropathic pain. Therefore, it is believed that the animal model, the evaluation method using the animal model, screening or evaluation of the drug, and the compound obtained by the evaluation described above will lead to great progress in the development of drugs for treating neuropathic pain.

INDUSTRIAL APPLICABILITY

The therapeutic agent for neuropathic pain in the present invention is useful for drug treatment for neuropathic pain. The neuropathic pain animal model of the present invention is a simple model which shows similar symptoms to those of human neuropathic pain, and by using the animal model of the present invention, the therapeutic effect of the drug against neuropathic pain can be determined efficiently. That is, the present invention can greatly advance the development of drugs for treating neuropathic pain.

The invention claimed is:
1. A method of treating neuropathic pain of a mammal actually suffering from neuropathic pain comprising administering to the mammal a therapeutically effective amount of a composition for the treatment of neuropathic pain comprising (−)-17-(cyclopropylmethyl)-3,14-dihydroxy-4,5α-epoxy-6β-[N-methyl-trans-3-(3-furyl)-acrylamido]morphinan or a pharmacologically acceptable acid addition salt thereof.

* * * * *

UNITED STATES PATENT AND TRADEMARK OFFICE
CERTIFICATE OF CORRECTION

| | | |
|---|---|---|
| PATENT NO. | : 8,637,539 B2 | Page 1 of 1 |
| APPLICATION NO. | : 11/206489 | |
| DATED | : January 28, 2014 | |
| INVENTOR(S) | : Nagase et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
First Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,637,539 B2  
APPLICATION NO. : 11/206489  
DATED : January 28, 2014  
INVENTOR(S) : Nagase et al.

Page 1 of 1

It is certified that error appears in the above-identified patent and that said Letters Patent is hereby corrected as shown below:

In the Claims

In Column 16

At line 60, claim 1, please change "14" to -- 14β --.

Signed and Sealed this
Twenty-fourth Day of June, 2014

Michelle K. Lee
*Deputy Director of the United States Patent and Trademark Office*